(12) United States Patent
Whittemore et al.

(10) Patent No.: US 7,785,587 B2
(45) Date of Patent: Aug. 31, 2010

(54) THERAPEUTIC METHODS FOR MUSCULAR OR NEUROMUSCULAR DISORDERS

(75) Inventors: Lisa-Anne Whittemore, East Walpole, MA (US); Xiangping Li, Wayland, MA (US)

(73) Assignee: Wyeth, Madison, NJ (US)

( * ) Notice: Subject to any disclaimer, the term of this patent is extended or adjusted under 35 U.S.C. 154(b) by 1735 days.

(21) Appl. No.: 10/858,353

(22) Filed: Jun. 1, 2004

(65) Prior Publication Data

US 2005/0014733 A1 Jan. 20, 2005

Related U.S. Application Data

(60) Provisional application No. 60/474,603, filed on Jun. 2, 2003.

(51) Int. Cl.
*A61K 39/395* (2006.01)
*A61K 31/00* (2006.01)
*A61K 38/00* (2006.01)

(52) U.S. Cl. .......................... 424/130.1; 514/1; 514/2; 530/350

(58) Field of Classification Search ........................ None
See application file for complete search history.

(56) References Cited

U.S. PATENT DOCUMENTS

| | | | |
|---|---|---|---|
| 4,370,976 A * | 2/1983 | Wanchik et al. ................ 602/22 |
| 5,130,141 A * | 7/1992 | Law et al. ..................... 424/548 |
| 5,562,717 A * | 10/1996 | Tippey et al. .................. 607/41 |
| 5,639,638 A | 6/1997 | Wozney et al. ............. 435/69.4 |
| 5,700,911 A | 12/1997 | Wozney et al. ............. 530/350 |
| 5,723,125 A | 3/1998 | Chang et al. |
| 5,756,457 A | 5/1998 | Wang et al. |
| 5,827,733 A | 10/1998 | Lee et al. |
| 5,914,234 A | 6/1999 | Lee et al. ...................... 435/7.1 |
| 5,994,618 A | 11/1999 | Lee et al. ....................... 800/18 |
| 6,004,937 A | 12/1999 | Wood et al. .................... 514/21 |
| 6,096,506 A | 8/2000 | Lee et al. ...................... 435/7.1 |
| 6,319,505 B1 * | 11/2001 | Aoki et al. ................. 424/236.1 |
| 6,340,668 B1 | 1/2002 | Celeste et al. .................. 514/12 |
| 6,368,597 B1 | 4/2002 | Strassmann et al. |
| 6,369,201 B1 | 4/2002 | Barker et al. |
| 6,372,454 B2 | 4/2002 | Duan et al. |
| 6,437,111 B1 | 8/2002 | Wozney et al. ............. 536/23.4 |
| 6,465,239 B1 | 10/2002 | Lee et al. |
| 6,607,884 B1 | 8/2003 | Lee et al. |
| 6,656,475 B1 | 12/2003 | Lee et al. |
| 6,696,260 B1 | 2/2004 | Lee et al. |
| 6,835,544 B2 | 12/2004 | Mathews et al. |
| 6,891,082 B2 | 5/2005 | Lee et al. |
| 7,192,717 B2 | 3/2007 | Hill et al. |
| 7,261,893 B2 | 8/2007 | Veldman et al. |
| 7,320,789 B2 | 1/2008 | Aghajanian et al. |
| 7,381,528 B2 | 6/2008 | Lee et al. |
| 7,393,682 B1 | 7/2008 | Lee et al. |
| 2002/0127234 A1 | 9/2002 | El Halawani et al. |
| 2002/0150577 A1 | 10/2002 | Lee et al. |
| 2002/0157125 A1 | 10/2002 | Lee et al. |
| 2003/0074680 A1 | 4/2003 | Lee et al. |
| 2003/0104406 A1 | 6/2003 | Wolfman et al. ............... 435/6 |
| 2003/0138422 A1 | 7/2003 | Aghajanian et al. ...... 424/145.1 |
| 2003/0162714 A1 | 8/2003 | Hill et al. ...................... 514/12 |
| 2003/0180306 A1 | 9/2003 | Hill et al. .................. 424/178.1 |
| 2004/0055027 A1 | 3/2004 | Lee et al. |
| 2004/0077053 A1 | 4/2004 | Lee et al. |
| 2004/0138118 A1 | 7/2004 | Wolfman et al. .............. 514/12 |
| 2004/0142382 A1 | 7/2004 | Veldman et al. .............. 435/7.1 |
| 2004/0181033 A1 | 9/2004 | Han et al. |
| 2004/0223966 A1 | 11/2004 | Wolfman et al. |
| 2005/0014733 A1 | 1/2005 | Whittemore |
| 2005/0043232 A1 | 2/2005 | Lee et al. |
| 2005/0257278 A1 | 11/2005 | Lee et al. |
| 2006/0240487 A1 | 10/2006 | Nowak et al. |
| 2006/0240488 A1 | 10/2006 | Nowak et al. |
| 2008/0178310 A1 | 7/2008 | Lee et al. |
| 2008/0213426 A1 | 9/2008 | Lee et al. |

FOREIGN PATENT DOCUMENTS

| | | |
|---|---|---|
| EP | 1 061 940 B1 | 12/2003 |
| EP | 1 444 985 A2 | 8/2004 |
| WO | WO 94/21681 | 9/1994 |
| WO | WO 94-26892 | 11/1994 |
| WO | WO 96-01845 | 1/1996 |
| WO | WO 98/33887 | 8/1998 |
| WO | WO98/35019 | 8/1998 |
| WO | WO 99/02667 | 1/1999 |
| WO | WO 99/06559 | 2/1999 |
| WO | WO 99/24058 | 5/1999 |
| WO | WO 99/24618 | 5/1999 |
| WO | WO 99/40181 | 8/1999 |
| WO | WO 99/45949 | 9/1999 |
| WO | WO 99/56768 | 11/1999 |
| WO | WO 00/11163 | 3/2000 |
| WO | WO 00/43781 | 7/2000 |
| WO | WO 01/05820 | 1/2001 |
| WO | WO 01-64888 A2 | 9/2001 |
| WO | WO 02/09641 A2 | 2/2002 |
| WO | WO 02/29105 A1 | 4/2002 |
| WO | WO 02/068650 A2 | 9/2002 |
| WO | WO 03/027248 A2 | 4/2003 |

(Continued)

OTHER PUBLICATIONS

Solomon and Bouloux, J. Endocr. 191: 349-360, 2006.*

(Continued)

*Primary Examiner*—Robert Landsman
*Assistant Examiner*—Gyan Chandra
(74) *Attorney, Agent, or Firm*—Finnegan, Henderson, Farabow, Garrett & Dunner, L.L.P.

(57) ABSTRACT

The disclosure provides methods for treating neuromuscular disorders in mammals. The disclosed methods include administering therapeutically effective amounts of a GDF-8 inhibitor and a corticosteroid to a subject susceptible to, or having, a neuromuscular disorder, so as to maintain desirable levels of muscle function.

69 Claims, 1 Drawing Sheet

FOREIGN PATENT DOCUMENTS

| WO | WO 03/037248 | 5/2003 |
|---|---|---|
| WO | WO 03/072714 | 9/2003 |
| WO | WO 03/072715 | 9/2003 |
| WO | WO 2004/024092 | 3/2004 |
| WO | WO 2004/037861 | 5/2004 |
| WO | WO2004/037861 | 5/2004 |
| WO | WO 2004/039948 | 5/2004 |
| WO | WO2004/039948 | 5/2004 |
| WO | WO2004-058988 A2 | 7/2004 |
| WO | WO 2004/108157 | 12/2004 |
| WO | WO 2006/020884 | 2/2006 |
| WO | WO 2006/102574 | 9/2006 |
| WO | WO 2006/107611 | 10/2006 |

OTHER PUBLICATIONS

McKenzie et al., Eur. J. Biochem. 269: 2010-2015, 2002.*
Reitter B., Brain and Dev.17: 39-43, 1995.*
Richard Robinson, Biology, vol. 3, pp. 108-109, 2002.*
Haidet et al., PNAS 105: 4318-4322, 2008.*
International Search Report, mailed Dec. 6, 2004 for International Patent Application No. PCT/US04/017049.
Granchelli et al., "Pre-Clinical Screening of Drugs Using the *mdx* Mouse," *Neuromuscular Disorders* 10:235-239 (2000).
Hudecki et al., "Strength and Endurance In the Therapeutic Evaluation of Prednisolone-Treated MDX Mice," *Res. Comm. Chem. Path. Pharma.* 79:45-60 (1993).
Lang et al., "Regulation of Myostatin by Glucocorticoids After Thermal Injury," *FASEB J.* 15:1807-1809 (2001).
Merlini et al., "Early Prednisone Treatment in Duchenne Muscular Dystrophy," *Muscle & Nerve* 27:222-227 (2003).
Muntoni et al., "Steroids in Duchenne Muscular Dystrophy: From Clinical Trials to Genomic Research," *Neuromuscular Disorders* 12:S162-S165 (2002).
Alexander et al., "Human Parathyroid Hormone 1-34 Reverses Bone Loss In Ovariectomized Mice," *J. Bone Miner. Res.* 16:1665-1673 (2001).
Alliel et al., "Testican, a Multidomain Testicular Proteoglycan Resembling Modulators of Cell Social Behaviour," *Eur. J. Biochem.* 214:347-350 (1993).
Amthor et al., "The Expression and Regulation of Follistatin and a Follistatin-like Gene During Avian Somite Compartmentalization and Myogenesis," *Dev. Biol.* 178:343-362 (1996).
Andersson et al., "Repeated In Vivo Determinations of Bone Mineral Density During Parathyroid Hormone Treatment in Ovariectomized Mice," *J. Endocrinol.* 170:529-537 (2001).
Attisano et al., "Activation of Signalling by the Activin Receptor Complex," *Mol. Cell. Biol.* 16:1066-1073 (1996).
Bartholin et al., "FLRG, an Activin-Binding Protein, is a New Target of TGFβ Transcription Activation Through Smad Proteins," *Oncogene* 20:5409-5419 (2001).
Brown et al., "Physicochemical Activation of Recombinant Latent Transforming Growth Factor-beta's 1, 2, and 3," *Growth Factors* 3:35-43 (1990).
D'Angelo et al., "Authentic Matrix Vesicles Contain Active Metalloproteases (MMP)," *J. Biol. Chem.* 276:11347-11353 (2001).
Derynck et al., "Human Transforming Growth Factor-β Complementary DNA Sequence and Expression in Normal and Transformed Cells," *Nature* 316:701-705 (1985).
Donoghue et al., "Rostrocaudal Gradient of Transgene Expression in Adult Skeletal Muscle," *Proc. Natl. Acad. Sci. U.S.A.* 88:5847-5851 (1991).
Gamer et al., "Gdf11 is a Negative Regulator of Chondrogenesis and Myogenesis in the Developing Chick Limb," *Dev. Biol.* 229:407-420 (2001).
Gentry et al., "The Pro Domain of Pre-Pro-Transforming Growth Factor β1 When Independently Expressed Is a Functional Binding Protein for the Mature Growth Factor," *Biochemistry* 29:6851-6857 (1990).

Hayette et al., "FLRG (Follistatin-Related Gene), A New Target of Chromosomal Rearrangement in Malignant Blood Disorders," *Oncogene* 16:2949-2954 (1998).
Hoodless et al., "Mechanisms and Function of Signaling by the TGFβ Superfamily," *Curr. Top. Microbiol. Immunol.* 228:236-272 (1998).
Huet et al., "Skeletal Muscle Cell Hypertrophy Induced by Inhibitors of Metalloproteases; Myostatin as a Potential Mediator," *Am. J. Physiol. Cell. Physiol.* 281:C1624-C1634 (2001).
Jiang et al., "Characterization and Identification of the Inhibitory Domain of GDF-8 Propeptide," *Biochem. Biophys. Res. Commun.* 315:525-531 (2004).
Kato, "A Secreted Tumor-Suppressor, mac25, with Activin-Binding Activity," *Mol. Med.* 6:126-135 (2000).
Kessler et al., "Bone Morphogenetic Protein-1: The Type I Procollagen C-Proteinase," *Science* 271:360-362 (1996).
Kingsley, D.M., "The TGF-β Superfamily: New Members, New Receptors, and New Genetic Tests of Function in Different Organisms," *Genes Dev.* 8:133-146 (1994).
Lee et al., "Analysis of Site-Directed Mutations in Human Pro-α2(I) Collagen Which Block Cleavage by the C-Proteinase," *J. Biol. Chem.* 265:21992-21996 (1990).
Li et al., "The C-Proteinase that Processes Procollagens to Fibrillar Collagens is Identical to the Protein Previously Identified as Bone Morphogenic Protein-1," *Proc. Natl. Acad. Sci. U.S.A.* 93:5127-5130 (1996).
Lin et al., "Expression Cloning of the TGF-β Type II Receptor, a Functional Transmembrane Serine/Threonine Kinase," *Cell* 68:775-785 (1992).
Liu et al., "Assigning the Positional Identity of Spinal Motor Neurons: Rostrocaudal Patterning of Hox-c Expression by FGFs, Gdf11, and Retinoids," *Neuron* 32:997-1012 (2001).
Lyons et al., "Proteolytic Activation of Latent Transforming Growth Factor-β from Fibroblast-Conditioned Medium," *J. Cell Biol.* 106:1659-1665 (1988).
Maeda et al., "Activation of Latent Transforming Growth Factor β1 by Stromelysin 1 in Extracts of Growth Plate Chondrocyte-Derived Matrix Vesicles," *J. Bone Miner. Res.* 16:1281-1290 (2001).
Maguer-Satta et al., "During Hematopoiesis, Expression of FLRG, a Novel Activin A Ligand, is regulated by TGF-β," *Exp. Hematol.* 29:301-308 (2001).
Marques et al., "Production of a DPP Activity Gradient in the Early Drosophilia Embryo through the Opposing Actions of the SOG and TLD Proteins," *Cell* 91:417-426 (1997).
Massagué et al., "Receptors for the TGFβ Family," *Cell* 69:1067-1070 (1992).
Massagué et al., "The TGF-β Family and its Composite Receptors," *Trends Cell Biol.* 4:172-178 (1994).
Massagué, "How Cells Read TGF-β Signals," *Nature Rev. Mol. Cell. Biol.* 1:169-178 (2000).
Massagué, "The Transforming Growth Factor-β Family," *Annu. Rev. Cell Biol.* 6:597-641 (1990).
McPherron et al., "Regulation of Anterior/Posterior Patterning of the Axial Skeleton by Growth/Differentiation Factor 11," *Nature Genet.* 22:260-264 (1999).
Miyazono et al., "Latent High Molecular Weight Complex of Transforming Growth Factor β1," *J. Biol. Chem.* 263:6407-6415 (1988).
Motamed, "Moleclues in Focus, SPARC (Osteonectin/BM-40)," *Int. J. Biochem. Cell Biol.* 31:1363-1366 (1999).
Moustakas et al., "Smad Regulation in TGF-β Signal Transduction," *J. Cell Sci.* 114:4359-4369 (2001).
Nakamura et al., "Follistatin, an Activin-Binding Protein, Associates with Heparan Sulfate Chains of Proteoglycans on Follicular Granulosa Cells," *J. Biol. Chem.* 266:19432-19437 (1991).
Nakamura et al., "Isolation and Characterization of Activin Receptor from Mouse Embryonal Carcinoma Cells," *J. Biol. Chem.* 267:18924-18928 (1992).
Nakashima et al., "Expression of Growth/Differentiation Factor 11, A New Member of the BMP/TGF β Superfamily During Mouse Embryogenesis," *Mech. Dev.* 80:185-189 (1999).
Ngo et al., In *The Protein Folding Problems and Tertiary Structure Prediction*, Merz et al., eds., *Brickhauser*, Springer Verlag, Boston, pp. 433-434 & 492-495 (1994).

Pappano et al., "Use of BMP1-TII1 Doubly Homozygous Null Mice and Proteomics to Identify and Validate In Vivo Substrates of Bone Morphogenetic Protein 1/Tolloid-Like Metalloproteinases," *Mol. Cell. Biol.* 23:4428-4438 (2003).

Patel et al., "Cloning and Early Dorsal Axial Expression of Flik, a Chick Follistatin-Related Gene: Evidence for Involvement in Dorsalization-Neural Induction," *Dev. Biol.* 178: 327-342 (1996).

Patthy et al., "Functions of Agrin and Agrin-Related Proteins," *Trends Neurosci.* 16:76-81 (1993).

Phillips et al., "Follistatin: A Multifunctional Regulatory Protein," *Front. Neuroendocrin.* 19:287-322 (1998).

Piccolo et al., "Cleavage of Chordin by Xolloid Metalloprotease Suggests a Role for Proteolytic Processing in the Regulation of Spemann Organizer Activity," *Cell* 91:407-416 (1997).

R&D Systems, Inc., "Recombinant Human Activin Receptor IIB-FC Chimera: Specifications and Use," Cat. No. 339-RB (2002).

Riley et al., "The Use of Single Nucleotide Polymorphisms in the Isolation of Common Disease Genes," *Pharmacogenomics* 1:39-47 (2000).

Sato et al., "Inhibition of Endothelial Cell Movement by Pericytes and Smooth Muscle Cells: Activation of a Latent Transforming Growth Factor-$\beta$1-Like Molecule by Plasmin During Co-Culture," *J. Cell Biol.* 109:309-315 (1989).

Schneyer et al., "Follistatin-Related Protein (FSRP): A New Member of the Follistatin Gene Family," *Mol. Cell. Endocrinol.* 180:33-38 (2001).

Scott et al., "Bone Morphogenetic Protein-1 Processes Probiglycan," *J. Biol. Chem.* 275:30504-30511 (2000).

Scott et al., "Mammalian BMP-1-Tolloid-Related Metalloproteinases, Including Novel Family Member Mammalian Tolloid-Like 2, Have Differential Enzymatic Activities and Distributions of Expression Relevant to Patterning and Skeletogenesis," *Dev. Biol.* 213:283-300 (1999).

Shibanuma et al., "Cloning From a Mouse Osteoblastic Cell Line of a Set of Transforming-Growth-Factor-$\beta$1-Regulated Genes, One of Which Seems to Encode a Follistatin-Related Polypeptide," *Eur. J. Biochem.* 217:13-19 (1993).

Sternberg et al., "Identification of Upstream and Intragenic Regulatory Elements that Confer Cell-Type-Restricted and Differentiation-Specific Expression on the Muscle Creatine Kinase Gene," *Mol. Cell. Biol.* 8:2896-2909 (1988).

Takahara et al., "Bone Morphogenetic Protein-1 and a Mammalian Tolloid Homologue (mTld) Are Encoded by Alternatively Spliced Transcripts Which Are Differentially Expressed in Some Tissues," *J. Biol. Chem.* 269:32572-32578 (1994).

Takahara et al., "Characterization of a Novel Gene Product (Mammalian Tolloid-like) with High Sequence Similarity to Mammalian Tolloid/Bone Morphogenetic Protein-1," *Genomics* 34:157-165 (1996).

Trexler et al., "Distinct Expression Pattern of Two Related Human Proteins Containing Multiple Types of Protease-Inhibitory Modules," *Biol. Chem.* 383:223-228 (2002).

Trexler et al., "A Human Protein Containing Multiple Types of Protease-Inhibitory Modules," *Proc. Natl. Acad. Sci. U.S.A.* 98:3705-3709 (2001).

Tsuchida et al., "Identification and Characterization of a Novel Follistatin-like Protein as a Binding Protein for the TGF-$\beta$ Family," *J. Biol. Chem.* 275:40788-40796 (2000).

Tsuchida et al., "Intracellular and Extracellular Control of Activin Function by Novel Regulatory Molecules," *Mol. Cell. Endocrinol.* 180:25-31 (2001).

Uzel et al., "Multiple Bone Morphogenetic Protein 1-Related Mammalian Metalloproteinases Process Pro-Lysyl Oxidase at the Correct Physiological Site and Control Lysyl Oxidase Activation in Mouse Embryo Fibroblast Cultures," *J. Biol. Chem.* 276:22537-22543 (2001).

Wakefield et al., "Latent Transforming Growth Factor-$\beta$ From Human Platelets," *J. Biol. Chem.* 263:7646-7654 (1988).

Wolfman et al., "Activation of Latent Myostatin by the BMP-1/Tolloid Family of Metalloproteinases," *Proc. Natl. Acad. Sci. U.S.A.* 100:15842-15846 (2003).

Wu et al., "Autoregulation of Neurogenesis by GDF-11," *Neuron* 37:197-207 (2003).

Wuytens et al., "Identification of Two Amino Acids in Activin A That Are Important for Biological Activity and Binding to the Activin Type II Receptors," *J. Biol. Chem.* 274:9821-9827 (1999).

Yu et al., "Cell Surface-Localized Matrix Metalloproteinase-9 Proteolytically Activates TGF-$\beta$ and Promotes Tumor Invasion and Angiogenesis," *Genes Dev.* 14:163-176 (2000).

Zwusen et al., "Characterization of a Rat $C_6$ Glioma-Secreted Follistatin-Related Protein (FRP) Cloning and Sequence of the Human Homologue," *Eur. J. Biochem.* 225:937-946 (1994).

Ashmore, et al., "Comparative Aspects of Muscle Fiber Types in Fetuses of the Normal and 'Double-Muscled' Cattle," *Growth* 38:501-506 (1974).

Bakker, et al., Duchenne and Becker Muscular Dystrophies. In *Diagnostic Criteria for Neuromuscular Disorders*, 2nd ed., Emery, ed., Royal Society of Medicine Press, 1998; pp. 1-4.

Bogdanovich, et al., "Functional Improvement of Dystrophic Muscle by Myostatin Blockade," *Nature* 420:418-421 (2002).

Bulfield, et al., "X Chromosome-Linked Muscular Dystrophy (*mdx*) in the Mouse," *Proc. Natl. Acad. Sci. U.S.A.* 81:1189-1192 (1984).

Emery, "The Muscular Dystrophies," *Lancet* 359:687-695 (2002).

Escolar, et al., "Pharmacologic and Genetic Therapy for Childhood Muscular Dystrophies," *Current Neurology and Neuroscience Reports* 1:168-174 (2001).

Gamer, et al., "A Novel BMP Expressed in Developing Mouse Limb, Spinal Cord, and Tail Bud Is a Potent Mesoderm Inducer in *Xenopus* Embryos," *Dev. Biol.* 208:222-232 (1999).

Gillis, "Multivariate Evaluation of the Functional Recovery Obtained by the Overexpression of Utrophin in Skeletal Muscles of the *mdx* Mouse," *Neuromuscular Disorders* 12:S90-S94 (2002).

Grady, et al., "Skeletal and Cardiac Myopathies in Mice Lacking Utrophin and Dystrophin: A Model for Duchenne Muscular Dystrophy," *Cell* 90:729-738 (1997).

Gonzalez-Cadavid, et al., "Organization of the Human Myostatin Gene and Expression in Healthy Men and HIV-Infected Men With Muscle Wasting," *Proc. Natl. Acad. Sci. U.S.A.*, 95:14938-14943 (1998).

Hamrick, et al., "Bone Mineral Content and Density in the Humerus of Adult Myostatin-Deficient Mice," *Calcif. Tissue Int.* 71(1):63-68 (2002).

Hamrick, et al., "Femoral Morphology and Cross-Sectional Geometry of Adult Myostatin-Deficient Mice," *Bone* 27:343-349 (2000).

Hill, et al., "The Myostatin Propeptide and the Follistatin-Related Gene are Inhibitory Binding Proteins of Myostatin in Normal Serum," *J. Biol. Chem.* 277:40735-40741 (2002).

Hill, et al., "Regulation of Myostatin in Vivo by Growth and Differentiation Factor-Associated Serum Protein-1: A Novel Protein with Protease Inhibitor and Follistatin Domains," *Mol. Endocrinol.* 17:1144-1154 (2003).

Hoffman, et al., "Conservation of the Duchenne Muscular Dystrophy Gene in Mice and Humans," *Science* 238:347-350 (1987).

Kambadur, et al., "Mutations in *myostatin* (GDF8) In Double-Muscled Belgian Blue and Piedmontese Cattle," *Genome Res.* 7:910-915 (1997).

Khurana, et al., "Pharmacological Strategies for Muscular Dystrophy," *Nat. Rev. Drug Disc.* 2:379-386 (2003).

Kim, et al., "Inhibition of Preadipocyte Differentiation by Myostatin Treatment in 3T3-L1 Cultures," *Biochem. Biophys. Res. Commun.* 281:902-906 (2001).

Lee, et al., "Regulation of Myostatin Activity and Muscle Growth," *Proc. Natl. Acad. Sci. U.S.A.* 98:9306-9311 (2001).

Matsuda, et al., "Visualization of Dystrophic Muscle Fibers in Mdx Mouse by Vital Staining with Evans Blue: Evidence of Apoptosis in Dystrophin-Deficient Muscle," *J. Biochem.* 118:959-964 (1995).

McPherron, et al., "Double Muscling in Cattle Due to Mutations in the Myostatin Gene," *Proc. Natl. Acad. Sci. U.S.A.* 94:12457-12461 (1997).

McPherron, et al., "Regulation of Skeletal Muscle Mass in Mice by a New TGF-$\beta$ Superfamily Member," *Nature* 387:83-90 (1997).

McPherron, et al., "Suppression of Body Fat Accumulation in Myostatin-Deficient Mice," *J. Clin. Invest.* 109:595-601 (2002).

Morrison, et al., "T-Cell-Dependent Fibrosis in the mdx Dystrophic Mouse," *Lab. Invest.* 80:881-891 (2000).

Schäcke, et al., "Mechanisms Involved in the Side Effects of Glucocorticoids," *Pharmacol. Ther.* 96:23-43 (2002).

Swatland, et al., "Fetal Development of the Double Muscled Condition in Cattle," *J. Anim. Sci.* 38:752-757 (1974).

Thies, et al., "GDF-8 Propeptide Binds to GDF-8 and Antagonizes Biological Activity by Inhibiting GDF-8 Receptor Binding," *Growth Factors* 18:251-259 (2001).

Torres, et al., "The Mutant mdx: Inherited Myopathy in the Mouse," *Brain* 110:269-299 (1987).

Umland, et al., "Review of the Molecular and Cellular Mechanisms of Action of Glucocorticoids for Use in Asthma," *Pulmonary Pharmacology & Therapeutics* 15:35-50 (2002).

Wagner, et al., "Loss of Mysostatin Attenuates Severity of Muscular Dystrophy in *mdx* Mice," *Ann. Neurol.* 52:832-836 (2002).

Whittemore, et al., "Inhibition of Myostatin in Adult Mice Increases Skeletal Muscle Mass and Strength," *Biochem. Biophys. Res. Commun.* 300:965-971 (2003).

Zimmers, et al., "Induction of Cachexia in Mice by Systemically Adminstered Myostatin," *Science* 296:1486-1488 (2002).

Zhu, et al., "Dominant Negative Myostatin Produces Hypertrophy Without Hyperplasia in Muscle" *FEBS Lett.* 474:71-75 (2000).

U.S. Appl. No. 10/689,677, filed Oct. 22, 2003, entitled "ActRIIB Fusion polypeptides and uses therefor".

Kun Ma et al. "Glucocorticoid-induced skeletal muscle atrophy is associated with upregulation of myostatin gene expression" Am J. Physio. Endocrinol. Metab. 285:E363-E371 (2003).

Casas et al. (1998) "Association of the Muscle Hypertrophy Locus with Carcass Traits in Beef Cattle," *J. Anim. Sci.* 76:468-473.

Ciarmela, et al. (2009) "Presence, Action, and Regulation of Myostatin in Rat Uterus and Myometrial Cells" *Endocrinology* 150(2):906-914.

Dickman, Steven (1997) "Gene Mutation Provides More Meat on the Hoof," *Science* 277:1922-1923.

Grobet et al. (1997) "A Deletion in the Bovine Myostatin Gene Causes the Double-Muscled Phenotype in Cattle," *Nature Genetics* 17:71-74.

Holzbaur et al. (2006) "A Deletion in the Bovine Myostatin Gene Causese the Double-Muscled Phenotype in Cattle," *Nature Genetics* 17:71-74.

McCroskery et al. (2003) "Myostatin negatively regulates satellite cell activation and self-renewal" *J. Cell Biol.* 162:1135-47.

McCroskery et al. (2005) "Improved muscle healing through enhanced regeneration and reducted fibrosos in myostain-null mice" *J. Cell Sci.* 118:3531-41.

McKnight, Steven L. (1997) "Gatekeepers of Organ Growth," *Proc. Natl. Acad. Sci. USA* 94:12249-12250.

Mennissier, F. (1982) "Present State of Knowledge About the Genetic Determination of Muscular Hypertrophy or the Double Muscled Trait in Cattle," *Muscle Hypertrophy of Genetic Origin and Its Uses to Improve Beef Production: A Seminar in CEC Programme of Coordinated Research on Beef Production* :387-428.

Springer et al., (2010) "Myostatin: Regulator of Muscle Wasting in Heart Failure and Treatment Target for Cardiac Cachexia" *Circulation* 121:354-356.

Thomas et al. (2000) "Myostatin, a Negative Regulator of Muscle Growth, Functions by Inhibiting Myoblast Proliferation" *J. Biol. Chem.* 275:40235-43.

Westhusin, Mark (1997) "From Mighty Mice to Mighty Cows," *Nature Genetics* 17:4-5.

\* cited by examiner

THERAPEUTIC METHODS FOR MUSCULAR OR NEUROMUSCULAR DISORDERS

This application claims priority to U.S. provisional application No. 60/474,603, filed on Jun. 2, 2003, which is incorporated herein by reference in its entirety.

FIELD OF THE INVENTION

The present invention relates to the field of clinical pathophysiology, and more particularly to methods for treating neuromuscular disorders, such as muscular dystrophies. The invention also relates to pharmaceutical formulations containing corticosteroids and inhibitors of growth and differentiation.

BACKGROUND OF THE INVENTION

Muscular dystrophies (MD) are progressive inherited neuromuscular disorders that are characterized by muscle wasting and weakness (Emery (2002) The Lancet, 359:687-695). Many forms of muscular dystrophies are fatal and currently incurable.

Duchenne muscular dystrophy (DMD) is the most common X-linked neuromuscular disease. The disease is caused by mutations in the DMD gene coding for dystrophin. Alteration or absence of this protein results in abnormal sarcolemmal membrane tearing. An abnormal variation in diameter of muscle fibers (atrophic and hypertrophic fibers) in proximal muscles and ongoing muscle damage are hallmarks of the disease. Damaged muscle releases the intracellular enzyme creatine kinase (CK). As a result, the serum CK levels in DMD patients are characteristically high (up to 10 times the normal). The pathophysiologic cascade is compounded by tissue inflammation, myofiber necrosis and replacement of muscle with fibrofatty tissue.

Another allelic variant of the DMD gene causes a milder form of MD known as Becker muscular dystrophy (BMD). BMD is clinically similar to DMD but the onset of symptoms occurs later in life.

Many pharmacological agents have been tried in MD but none has proved effective in arresting the course of the disease. The current modality of treatment is still in the realm of physical medicine and rehabilitation.

A number of trials using corticosteroids (e.g., prednisone and/or its derivatives) have demonstrated improvement in individuals with MD, particularly in the short-term. Although the exact mechanism by which corticosteroids alleviate the disease phenotype is unclear, corticosteroids are thought to act by reducing inflammation, suppressing the immune system, improving calcium homeostasis, upregulating expression of compensatory proteins, and increasing myoblast proliferation (Khurana et al. (2003) Nat. Rev. Drug Discovery 2:279-386). However, corticosteroids administered over time can induce muscle atrophy, which primarily affects proximal muscles—the very same muscles that are affected in DMD and BMD. The corticosteroid-induced muscle and other side effects may limit the long-term effectiveness of corticosteroid therapy.

GDF-8 is a member of the TGF-β superfamily and functions as a negative regulator of muscle growth. Similarly to other members of the superfamily, GDF-8 is synthesized as a precursor molecule, but prior to secretion, it is cleaved into the N-terminal inhibitory propeptide and C-terminal active mature GDF-8. Propeptide may remain bound to GDF-8 thereby inhibiting the biological activity of mature GDF-8. Propeptide must dissociate from the complex for GDF-8 to bind to activin type II receptor (ActRIIB). Upon binding, ActRIIB initiates a signaling cascade, ultimately leading to the inhibition of myoblast progression. Antibody-mediated inhibition of GDF-8 in vivo has been shown to significantly increase skeletal muscle size in normal adult mice (Whittemore et al. (2003) BBRC, 300:965-971) and to alleviate the dystrophic phenotype in the mdx mouse model of DMD (Bogdanovich et al. (2002) Nature, 420(28):418-421).

SUMMARY OF THE INVENTION

It is one of the objects of the present invention to provide methods and compositions for treating disorders characterized by or associated with a risk of diminution of muscle function. Additional objects of the invention will be set forth in part in the following description, and in part will be understood from the description, or may be learned by practice of the invention.

The present invention is based, in part, on the discovery and demonstration that, in a mouse model of DMD, treatment by administration of a neutralizing anti-GDF-8 antibody and prednisone is more effective in increasing muscle mass and strength relative to treatment with prednisone alone. The invention is further based, in part, on the discovery and demonstration that administration of anti-GDF-8 antibody with prednisone reduces prednisone-induced muscle atrophy.

Accordingly, the present invention provides methods for treating neuromuscular disorders in mammals. The disclosed methods include administering to a subject susceptible to or having a neuromuscular disorder therapeutically effective amounts of at least one GDF-8 inhibitor and at least one corticosteroid so as to maintain desirable levels of muscle integrity or function as assessed by, for example, serum concentration of creatine kinase (CK), muscle histology, tissue imaging, activities of daily living, muscle strength and/or mass. The populations treated by the methods of the invention include, but are not limited to, patients having or at risk of developing muscular dystrophy such as, for example, DMD or BMD, and subjects undergoing corticosteroid therapy for these or other disorders.

The invention further provides methods of treating muscle weakness and methods of treating corticosteroid-induced muscle atrophy. The invention includes methods of treating cardiomyopathy.

Methods of administration and compositions used in the methods of the inventions are provided. In the disclosed methods, a GDF-8 inhibitor and a corticosteroid are administered concurrently or over alternating overlapping or non-overlapping intervals.

GDF-8 inhibitors, used in the methods of the present invention, include, but are not limited to, antibodies to GDF-8; antibodies to GDF-8 receptors; soluble GDF-8 receptors and fragments thereof (e.g., ActRIIB fusion polypeptides as described in U.S. patent application Ser. No. 10/689,677, including soluble ActRIIB receptors in which ActRIIB is joined to the Fc portion of an immunoglobulin); GDF-8 propeptide and modified forms thereof (e.g., as described in WO 02/068650 or U.S. patent application Ser. No. 10/071,499, now U.S. Pat. No. 7,202,210, including forms in which GDF-8 propeptide is joined to the Fc portion of an immunoglobulin and/or form in which GDF-8 is mutated at an aspartate (asp) residue, e.g., asp-99 in murine GDF-8 propeptide and asp-100 in human GDF-8 propeptide); a small molecule inhibitor of GDF-8; follistatin (e.g., as described in U.S. Pat. No. 6,004,937) or follistatin-domain-containing proteins (e.g., GASP-1 or other proteins as described in U.S. patent application Ser. Nos. 10/369,736 and 10/369,738, now U.S. Pat. Nos. 7,192,717 and 7,572,763); and modulators of metalloprotease activity that affect GDF-8 activation, as described in U.S. patent application Ser. No. 10/662,438.

In some embodiments, the GDF-8 inhibitor is a monoclonal antibody or a fragment thereof that blocks GDF-8 binding to its receptor. Nonlimiting illustrative embodiments include a nonhuman monoclonal anti-GDF-8 antibody, e.g., murine monoclonal antibody JA-16 (as described in U.S. patent application Ser. No. 10/253,532, now U.S. Pat. No. 7,320,789; deposited with American Type Culture Collection (ATCC), 10801 University Blvd., Manassas, Va., USA, on Apr. 18, 2002, under the requirements of the Budapest Treaty and accorded ATCC Deposit No. PTA-4236); derivatives thereof, e.g., humanized antibody; and fully human monoclonal anti-GDF-8 antibodies (e.g., Myo29, Myo28, and Myo22, as described in U.S. patent application Ser. No. 10/688,925, now U.S. Pat. No. 7,261,893; ATCC Deposit Nos. PTA-4741, PTA-4740, and PTA-4739, respectively) or derivatives thereof.

Corticosteroids, used in the method of the invention include, but are not limited to, beclomethasone dipropionate, budesonide, cortisol, dexamethasone, fluticason propionate, mometasone furoate, prednisone, triamcinolone acetonide, and derivatives thereof.

It is to be understood that both the foregoing general description and the following detailed description are exemplary and explanatory only and are not restrictive of the invention as claimed.

BRIEF DESCRIPTION OF THE FIGURES

FIGS. 1A and 1B depict results of a histological analysis of diaphragm muscle from mdx mice treated for four weeks with anti-GDF-8 neutralizing antibody JA-16 (60 mg/kg, once weekly) and prednisone (2 mg/kg, 3 times a week), prednisone alone, or vehicle control alone.

DETAILED DESCRIPTION OF THE INVENTION

I. Definitions

In order that the present invention may be more readily understood, certain terms are first defined. Additional definitions are set forth throughout the detailed description.

The term "antibody," as used herein, refers to an immunoglobulin or a part thereof and encompasses any polypeptide comprising an antigen-binding site regardless of the source, method of production, and other characteristics. As a nonlimiting example, the term "antibody" includes human, orangutan, mouse, rat, goat, sheep, and chicken antibodies. The term includes but is not limited to polyclonal, monoclonal, monospecific, polyspecific, non-specific, humanized, single-chain, chimeric, synthetic, recombinant, hybrid, mutated, and CDR-grafted antibodies. For the purposes of the present invention, it also includes, unless otherwise stated, antibody fragments such as Fab, F(ab')2, Fv, scFv, Fd, dAb, and other antibody fragments that retain the antigen-binding function.

Antibodies can be made, for example, via traditional hybridoma techniques (Kohler and Milstein (1975) Nature, 256: 495-499), recombinant DNA methods (U.S. Pat. No. 4,816, 567), or phage display techniques using antibody libraries (Clackson et al. (1991) Nature, 352: 624-628; Marks et al. (1991) J. Mol. Biol., 222: 581-597). For various other antibody production techniques, see Antibodies: A Laboratory Manual, eds. Harlow et al., Cold Spring Harbor Laboratory, 1988.

The term "antigen-binding domain" refers to the part of an antibody molecule that comprises the area specifically binding to or complementary to a part or all of an antigen. Where an antigen is large, an antibody may only bind to a particular part of the antigen. The epitope or antigenic determinant is a portion of an antigen molecule that is responsible for specific interactions with the antigen-binding domain of an antibody. An antigen-binding domain may be provided by one or more antibody variable domains (e.g., a so-called Fd antibody fragment consisting of a VH domain). An antigen-binding domain comprises an antibody light chain variable region (VL) and an antibody heavy chain variable region (VH).

The term "anti-GDF-8 antibody," or "antibody to GDF-8," refers to any antibody that specifically binds to at least one epitope of GDF-8. The terms "GDF-8 receptor antibody" and "antibody to a GDF-8 receptor" refer to any antibody that specifically binds to at least one epitope of a GDF-8 receptor, such as ActRIIB. The term "neutralizing antibody" refers to an antibody that is a GDF-8 inhibitor.

The term "specific interaction," or "specifically binds," or the like, means that two molecules form a complex that is relatively stable under physiologic conditions. The term is also applicable where, e.g., an antigen-binding domain is specific for a particular epitope, which may be present on a number of antigens. Specific binding is characterized by a high affinity and a low to moderate capacity. Nonspecific binding usually has a low affinity with a moderate to high capacity. Typically, the binding is considered specific when the affinity constant $K_a$ is higher than $10^6$ M$^{-1}$, than $10^7$ M$^{-1}$, or preferably higher than $10^8$ M$^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc.

The term "muscle function" refers to the ability of muscle to perform a physiologic function, such as contraction as measured by the amount of force generated during either twitch or tetanus. Other methods for assessing muscle function are well known in the art and include, but are not limited to, measurements of muscle mass, grip strength, serum CK level, activities of daily living, motion or strength tests, tissue histology (e.g., E&A staining, or collagen III staining), or tissue imaging. Nonlimiting illustrative methods for assessing muscle function are set forth in the Examples.

The term "GDF-8" refers to a specific growth and differentiation factor-8 and, where appropriate, factors that are structurally or functionally related to GDF-8, for example, BMP-11 and other factors belonging to the TGF-β superfamily. The term refers to the full-length unprocessed precursor form of GDF-8 as well as the mature and propeptide forms resulting from post-translational cleavage. The term also refers to any fragments and variants of GDF-8 that maintain at least some biological activities associated with mature GDF-8, as discussed herein, including sequences that have been modified. The present invention relates to GDF-8 from all vertebrate species, including, but not limited to, human, bovine, chicken, mouse, rat, porcine, ovine, turkey, baboon, and fish (for sequence information, see, e.g., McPherron et al. (1997) Proc. Nat. Acad. Sci. U.S.A., 94: 12457-12461).

The term "mature GDF-8" refers to the protein that is cleaved from the carboxy-terminal domain of the GDF-8 precursor protein. The mature GDF-8 may be present as a monomer, homodimer, or in a GDF-8 latent complex. Depending on conditions, mature GDF-8 may establish equilibrium between any or all of these different forms. In its biologically active form, the mature GDF-8 is also referred to as "active GDF-8."

The term "GDF-8 propeptide" refers to the polypeptide that is cleaved from the amino-terminal domain of the GDF-8 precursor protein. The GDF-8 propeptide is capable of binding to the propeptide binding domain on the mature GDF-8.

The term "GDF-8 latent complex" refers to the complex of proteins formed between the mature GDF-8 homodimer and the GDF-8 propeptide. It is believed that two GDF-8 propeptides associate with two molecules of mature GDF-8 in the homodimer to form an inactive tetrameric complex. The latent complex may include other GDF inhibitors in place of or in addition to one or more of the GDF-8 propeptides.

The term "GDF-8 activity" refers to one or more of physiologically growth-regulatory or morphogenetic activities associated with active GDF-8 protein. For example, active GDF-8 is a negative regulator of skeletal muscle mass. Active GDF-8 can also modulate the production of muscle-specific enzymes (e.g., creatine kinase), stimulate myoblast proliferation, and modulate preadipocyte differentiation to adipocytes. Exemplary procedures for measuring GDF-8 activity in vivo and in vitro are found in U.S. patent application Ser. No. 10/688,925, now U.S. Pat. No. 7,261,893 for example.

As used herein, "GDF-8 inhibitor" generally refers to any compound that downregulates the activity of GDF-8, and includes any agent capable of inhibiting activity, expression, processing, or secretion of GDF-8. A GDF-8 inhibitor may, for example, affect stability of or conversion of the precursor molecule to the active, mature form; interfere with the binding of GDF-8 to one or more receptors; or interfere with intracellular signaling of the GDF-8 receptor ActRIIB. Such inhibitors include proteins, antibodies, peptides, peptidomimetics, ribozymes, anti-sense oligonucleotides, double-stranded RNA, and other small molecules, which specifically inhibit GDF-8. Such inhibitors are said to "inhibit," "neutralize," or "reduce" the biological activity of GDF-8.

The terms "neutralize," "neutralizing," "inhibitory," and their cognates refer to a reduction in the activity of GDF-8 by a GDF-8 inhibitor, relative to the activity of GDF-8 in the absence of the same inhibitor. The reduction in activity is preferably at least about 10%, 20%, 30%, 40%, 50%, 60%, 70%, 80%, 90%, or higher. The methods for assessing neutralizing or inhibitory biological activity of GDF-8 inhibitors are known in the art, and can be performed, for example, using the ActRIIB assay (e.g., as described in Whittemore et al. (2003) BBRC, 300:965-97; or U.S. patent application Ser. No. 10/253,532, now U.S. Pat. No. 7,320,789) and the RGA assays (as described in Thies (2001) Growth Factors, 18:251-259 or U.S. patent application Ser. No. 10/253,532 now U.S. Pat. No. 7,320,789).

The term "therapeutically effective dose," or "therapeutically effective amount," refers to that amount of a compound that results in prevention, reduction in the risk of occurrence, or amelioration of symptoms in a patient, or a desired biological outcome, e.g., improved muscle function, delayed onset of clinical symptoms, etc. The effective amount can be determined as described in the subsequent sections.

The terms "treatment," "therapeutic method," and their cognates refer to treatment or prophylactic/preventative measures. Those in need of treatment may include individuals already having a particular medical disorder as well as those who may ultimately acquire the disorder. Treatment includes any reduction in any symptom of a disorder described in this application. In addition to a reduction or lessening of symptoms, treatment also includes maintaining a patient's current status when worsening is expected, or preventing the occurrence of a symptom in an individual in which the onset of a symptom, disorder, or disease is expected. Treatment may include a decrease or reduction in one or more physiologic function from normal. It may also include a decrease compared to expected symptoms or expected progression of the condition, disorder, or disease.

II. Components for Use in the Methods of the Invention

In the methods of the present invention, one or more GDF-8 inhibitors are used in combination with one or more corticosteroids.

A. GDF-8 Inhibitors

GDF-8 inhibitors, used in the methods of the present invention, include, but are not limited to, antibodies to GDF-8; antibodies to GDF-8 receptors; soluble GDF-8 receptors and fragments thereof (e.g., ActRIIB fusion polypeptides as described in U.S. patent application Ser. No. 10/689,677, including soluble ActRIIB receptors in which ActRIIB is joined to the Fc portion of an immunoglobulin); GDF-8 propeptide and modified forms thereof (e.g., as described in WO 02/068650 or U.S. patent application Ser. No. 10/071,499, now U.S. Pat. No. 7,202,210, including forms in which GDF-8 propeptide is joined to the Fc portion of an immunoglobulin and/or forms in which GDF-8 is mutated at an aspartate (asp) residue, e.g., asp-99 in murine GDF-8 propeptide and asp-100 in human GDF-8 propeptide); follistatin (e.g., as described in U.S. Pat. No. 6,004,937) or follistatin-domain-containing proteins (e.g., GASP-1 or other proteins as described in U.S. patent application Ser. Nos. 10/369,736 and 10/369,738, now U.S. Pat. Nos. 7,192,717 and 7,572,763); and modulators of metalloprotease activity that affect GDF-8 activation, as described in U.S. patent application Ser. No. 10/662,438.

In some embodiments, the GDF-8 inhibitor is a monoclonal antibody or a fragment thereof that blocks GDF-8 binding to its receptor. Nonlimiting illustrative embodiments include a nonhuman monoclonal anti-GDF-8 antibody, e.g., murine monoclonal antibody JA-16 (as described in U.S. patent application Ser. No. 10/253,532, now U.S. Pat. No. 7,320,789; ATCC Deposit No. PTA-4236); derivatives thereof, e.g., humanized antibodies; and fully human monoclonal anti-GDF-8 antibodies (e.g., Myo29, Myo28, and Myo22, as described in U.S. patent application Ser. No. 10/688,925, now U.S. Pat. No. 7,261,893; ATCC Deposit Nos. PTA-4741, PTA-4740, and PTA-4739, respectively), or derivatives thereof.

In some embodiments, the GDF-8 inhibitor blocks GDF-8 from binding to its receptor, by binding to GDF-8 or to the GDF-8 receptor. In various embodiments, the GDF-8 inhibitor is an anti-GDF-8 antibody that has the affinity to GDF-8, expressed as an affinity constant ($K_a$), wherein $K_a$ is at least $10^5 M^{-1}$, $10^6 M^{-1}$, $10^7 M^{-1}$, $10^8 M^{-1}$, $10^9 M^{-1}$, $10^{10} M^{-1}$, $10^{11} M^{-1}$, or $10^{12} M^{-1}$. Also contemplated for use in humans are inhibitors that are humanized forms and derivatives of non-human antibodies derived from any vertebrate species described in patent applications cited herein, or in Antibody Engineering, ed. Borrebaeck, 2nd ed., Oxford University Press, 1995; and Antibodies: A Laboratory Manual, eds. Harlow et al., Cold Spring Harbor Laboratory, 1988.

B. Corticosteroids

Corticosteroids used in the methods of the present invention, include, but are not limited to, beclomethasone dipropionate, budesonide, cortisol, dexamethasone, fluticason propionate, prednisone, mometasone furoate, triamcinolone acetonide, and derivatives thereof.

Pharmaceutically acceptable salts of compounds disclosed herein can also be used.

Corticosteroids are available commercially in various pharmaceutical formulations (Physician's Desk Reference (PDR) 2003, 57th ed., Medical Economics Company, 2002). For example, oral formulations are commercially available for cortisone, hydrocortisone (Cortef®), prednisone (Deltasone®, Meticorten®, Orasone®), prednisolone (Delta-Cortef®, Pediapred®, Prelone®), triamcinolone (Aristocort®, Kenacort®), methylprednisolone (Medrol®), dexamethasone (Decadron®, Dexone®, Hexadrol®), betamethasone (Celestone®), and deflazacort (Calcort®). Other formulations of these and other corticosteroids can be used in the methods of the invention.

C. Therapeutic and Prophylactic Methods

The invention provides method of treating mammalian subjects, including methods to treat loss of muscle function, muscle weakness, and/or corticosteroid-induced muscle atrophy.

Methods of the invention comprise administering to the mammal a therapeutically effective amount of at least one GDF-8 inhibitor and a therapeutically effective amount of at least one corticosteroid in the amounts and for a period of time sufficient to treat at least one of loss of muscle function, muscle mass, muscle weakness, muscle atrophy, or cardiomyopathy. The methods can be used for treating neuromuscular disorders such as muscular dystrophies. In some embodiments, muscle function is improved relative to the same treatment either in the absence of the GDF-8 inhibitor or the corticosteroid. The muscles treated include, but are not limited to, gastrocnemius, tibialis, anterior, quadriceps, extensor digitorum, cardiac muscle, or diaphragm muscle.

Neuromuscular disorders include, but are not limited to, any acute or chronic disease or disorder that compromises muscle function, causes muscular injury, or otherwise causes a diminution in muscle mass and/or function. A wide variety of diseases or disorders is known and includes, for example, muscular dystrophies such Duchenne muscular dystrophy, Becker muscular dystrophy, Emery Dreifuss muscular dystrophy, limb girdle muscular dystrophy, rigid spine syndrome, Ulirich syndrome, Fukuyama muscular dystrophy, Walker-Warburg syndrome, muscle-eye-brain disease, facioscapulohumeral muscular dystrophy, congenital muscular dystrophy, myotonic dystrophy (Steinert's disease), non-dystrophic myotonia, periodic paralyses spinal muscular atrophy, familial amytrophic lateral sclerosis, hereditary motor and sensory neuropathy, Charcot-Marie-Tooth disease, chronic inflammatory neuropathy, distal myopathy, myotubular/centronuclear myopathy, nemaline myopathy, mini core disease, central core disease, desminopathy, inclusion body myositis, mitochondrial myopathy, congenital myasthenic syndrome, post-polio muscle dysfunction, and disorders described in Emery (2002) The Lancet, 359:687-695; and Khurana et al. (2003) Nat. Rev. Drug Disc., 2:379-386. Patients may exhibit mild, moderate or severe muscle weakness, muscle wasting, and effects on independent ambulation associated with such a disorder. Patients having or at risk for developing these disorder will benefit from GDF-8 inhibitor and a corticosteroid.

In general, a patient who will benefit from coadministration of a GDF-8 inhibitor and a corticosteroid is one who exhibits a 2-10-fold or higher increase in the serum CK activity, a positive family history, an abnormal variation in the diameter of muscle fibers, a deficiency in dystrophin or a mutation in the dystrophin gene, loss of muscle mass, muscle weakness, cardiomyopathy, and/or loss of muscle strength. The diagnostic procedures, including the appropriate genetic testing, are described in Diagnostic Criteria for Neuromuscular Disorders, ed. Emery, 2nd ed., Royal Society of Medicine Press, 1997. The combination treatment can be also beneficial to subjects undergoing corticosteroid therapy for disorders other than neuromuscular disorders and/or subjects with a history of a long-term corticosteroid use so long these subjects exhibit, or are at risk of diminution of muscle function such as characterized by muscle weakness, loss of muscle mass, and/or muscle atrophy, etc. Examples of disorders for which corticosteroid therapy is often used include, but are nor limited to, asthma, allergy, arthritis, dermatologic disorders (e.g., inflammatory dermatoses, eczema, psoriasis, etc), lupus erythematosus, and other chronic inflammatory conditions.

Methods of administration and compositions used in the methods of the inventions are provided. Administration is not limited to any particular delivery system and may include, without limitation, parenteral (including subcutaneous, intravenous, intramedullary, intraarticular, intramuscular, or intraperitoneal injection) rectal, topical, transdermal, or oral (for example, in capsules, suspensions, or tablets). Administration to an individual may occur in a single dose or in repeat administrations, and in any of a variety of physiologically acceptable salt forms, and/or with an acceptable pharmaceutical carrier and/or additive as part of a pharmaceutical composition. Physiologically acceptable salt forms and standard pharmaceutical formulation techniques and excipients are well known to persons skilled in the art (e.g., as described in Physician's Desk Reference (PDR) 2003, 57th ed., Medical Economics Company, 2002; and Remington: The Science and Practice of Pharmacy, eds. Gennado et al., 20th ed, Lippincott, Williams & Wilkins, 2000).

A GDF-8 inhibitor and a corticosteroid are administered concurrently or consecutively over overlapping or nonoverlapping intervals. In the sequential administration, the GDF-8 inhibitor and the corticosteroid can be administered in any order. In some embodiments, the length of an overlapping or nonoverlapping interval is more than 2, 4, 6, 12, 24, or 48 weeks.

For corticosteroids, the prescribing physician routinely selects the dosage and regimen. For example, prednisone is used at about 0.1-2 mg per kilogram of body weight per day, and most commonly at 0.5-1 mg/kg/day, e.g., 0.75 mg/kg/day. The corticosteroid may be administered at average weekly doses of approximately 1-14 mg/kg body weight, including approximately 1, 2, 5, 7, 10, 12, or 15 mg/kg body weight per week, and the prescribing physician may select a frequency of administration as appropriate. Single dose, continuous or periodic corticosteroid administration may be selected, including administration at hourly, daily, bi-weekly, weekly, or other periodic intervals. Preferably, corticosteroids are administered orally or by injection 1-4 times per day. Corticosteroid dosage may be optimized as a combination therapy, and dosage may be lowered to reduce significant side effects of administration.

The GDF-8 inhibitors can be administered alone or in a mixture with a corticosteroid or another compound. GDF-8 inhibitors can be administered at a dose of approximately from 1 µg/kg to 25 mg/kg, depending on physiology, the severity of the symptoms and the progression of the disease. Single dose, continuous, or periodic administration may be selected, with intervals between GDF-8 inhibitor doses chosen from hourly, daily, bi-weekly weekly, weekly, bimonthly, monthly, or other appropriate intervals. For example, GDF-8 inhibitors such as antibodies may be administered in an outpatient setting by weekly administration at about 0.1-10 mg/kg dose by intravenous (IV) infusion, intraperitoneal, or subcutaneous injection. In general, the appropriate therapeutically effective dose of a GDF-8 inhibitor is selected by a treating clinician and would range approximately from 1 µg/kg to 20 mg/kg, from 1 µg/kg to 10 mg/kg, from 1 µg/kg to 1 mg/kg, from 10 µg/kg to 1 mg/kg, from 10 µg/kg to 100 µg/kg, from 100 µg to 1 mg/kg, and from 500 µg/kg to 5 mg/kg. Exemplary effective doses of GDF-8 inhibitor include approximately 0.1, 0.3, 0.5, 1, 5, 10, or 20 mg/kg/wk. Additionally, specific dosages indicated in the Examples or in the Physician's Desk Reference (PDR) 2003, 57th ed., Medical Economics Company, 2002, can be used.

D. Methods of Testing Compounds for Therapeutic Efficacy

The invention further provides methods for testing in an animal, e.g., a rodent or a primate, whether a therapeutic compound is efficacious when administered in combination with at least one GDF-8 inhibitor and at least one corticosteroid. In some embodiments, the method of evaluating the efficacy of a compound comprises: administering the compound to a first animal in combination with a GDF-8 inhibitor and a corticosteroid; administering the GDF-8 inhibitor and the corticosteroid to a second animal; determining the level of muscle function in the first and in the second animal after the administrations; and comparing the levels of muscle function. If the level in the first animal is lower than the level in the second animal, it indicates that the compound or the combination is efficacious.

In other embodiments, the compound may be evaluated for efficacy in treatment of muscular dystrophy when administered in combination with a GDF-8 inhibitor and/or a corticosteroid.

Several animal models are available for such evaluative purposes. For example, the mdx model has been described, for example, by Torres et al. (1987) Brain, 110:269-299, and Hoffman et al. (1987) Science, 238:347-350. Extremely high levels of CK are consistently noted with dystrophin-deficiency in mdx mice and DMD humans due to sarcolemmal damage (Bulfield et al. (1984) Proc. Natl. Acad. Sci. USA, 81:1189-1192; and Matsuda et al. (1995) J. Biochem. (Tokyo), 118: 959-64). As another example, two other animal models can be used: utr−/−mdx mice (Gillis (2002) Neuromuscul. Disord., 12(1):90-84; and Deconick et al. (1997) Cell, 90:729-738) and nu−/−mdx mice (Morrison et al. (2000) Lab. Invest., 80:881-891).

EXAMPLE

Example 1

Effect of GDF-8 Neutralizing Antibody on Dystrophic Muscle

The ability of in vivo inhibition of GDF-8 to ameliorate muscular dystrophy was tested in the mdx mouse model of DMD. Five to seven week old male C57BL/10ScSn-mdx/j mice (Jackson Laboratory, Bar Harbor, Me.) were treated with weekly intraperitoneal injections of the GDF-8 neutralizing murine antibody JA-16 (60 mg/kg, double dosing at first week, n=11), and vehicle alone (control group, n=10) for 12 weeks. These mice were also compared to mice of the same background strain (C57BL/10, n=12) without the dystrophin deficiency.

The body weight was monitored before, during and after treatment. Mice in the treatment group gained weight relative to mice in the vehicle control group. Results are shown in Table 1.

TABLE 1

| | Total body weight (g) Average values with SEM | | |
|---|---|---|---|
| Week of trial | JA-16 (mdx) | vehicle control (mdx) | vehicle control (non-mdx) |
| 0 | 21.92 +/− 0.42 | 22.51 +/− 0.36 | 19.18 +/− 0.40 |
| 4 | 27.82 +/− 0.43 | 26.76 +/− 0.60 | 24.14 +/− 0.27 |
| 8 | 29.59 +/− 0.54 | 28.49 +/− 0.58 | 25.31 +/− 0.28 |
| 12 | 32.42 +/− 0.57 | 31.12 +/− 0.73 | 27.17 +/− 0.39 |

Mice were also subjected to a grip test after 6 to 10 weeks of dosing. Mice in the treatment group at four and ten weeks had 9% (p=0.09) and 19% (p<0.05) respectively greater grip strength than mice in the vehicle control groups. Results are shown in Table 2.

TABLE 2

| | Grip strength (lb) Average values with SEM | | |
|---|---|---|---|
| Week of trial | JA-16 (mdx) | vehicle control (mdx) | vehicle control (non-mdx) |
| 6 | 0.261 +/− 0.011 | 0.239 +/− 0.006 | 0.239 +/− 0.011 |
| 10 | 0.249 +/− 0.006 | 0.210 +/− 0.014 | 0.247 +/− 0.010 |

To quantify the difference in muscle mass between treatment and vehicle control, animals were sacrificed and quadriceps and gastrocnemius muscles dissected out and weighed. Quadriceps muscles from the treated group of animals weighed 13% more than controls (0.371±0.009 vs. 0.317±0.008 g; p<0.05). Gastrocnemius muscles from the treated group of animals weighed 17% more than controls (0.223±0.008 vs. 0.197±0.005 g; p<0.0005).

Example 2

Effect of GDF-8 Neutralizing Antibody and Prednisone on Normal and Dystrophic Muscle Male C57BL/10ScSn-mdx/j and C57BL/10 (Jackson Laboratory, Bar Harbor, Me.). Mouse monoclonal anti-GDF-8 antibody JA-16, prednisone (P-9901, Sigma), or vehicle (peanut oil) was injected starting at age 5-7 weeks for 4 weeks. Mice were intraperitoneally (IP) injected with JA-16 at a dose of 60 mg/kg per week (double dosing at first week), or subcutaneously (SC) injected with prednisone at 2 mg/kg, 3 times a week.

The body weight and grip strength were monitored before, during and after treatment. Results are shown in Table 3 and Table 4, respectively.

TABLE 3

Total body weight (average ± SEM, g)

| Week of trial | Prednisone + JA-16 (mdx) | Prednisone (mdx) | vehicle control (mdx) | vehicle control (non-mdx) |
|---|---|---|---|---|
| 0 | 17.7 ± 1.6 | 17.6 ± 1.8 | 16.0 ± 1.9 | 19.2 ± 0.4 |
| 1 | 22.1 ± 1.4 | 20.9 ± 1.8 | 19.1 ± 2.1 | 22.4 ± 0.3 |
| 2 | 25.9 ± 1.2 | 24.2 ± 1.6 | 23.7 ± 1.4 | 23.8 ± 0.4 |
| 3 | 26.5 ± 1.1 | 24.7 ± 1.5 | 24.8 ± 1.2 | 24.9 ± 0.4 |
| 4 | 28.1 ± 1.2 | 25.9 ± 1.6 | 25.7 ± 1.4 | 25.6 ± 0.5 |

TABLE 4

Grip strength (average ± SEM, lb)

| Week of trial | Prednisone + JA-16 (mdx) | Prednisone (mdx) | vehicle control (mdx) | vehicle control (non-mdx) |
|---|---|---|---|---|
| 0 | 0.161 ± 0.018 | 0.144 ± 0.010 | 0.164 ± 0.014 | 0.164 ± 0.009 |
| 3 | 0.219 ± 0.019 | 0.177 ± 0.006 | 0.168 ± 0.005 | 0.212 ± 0.010 |
| 4 | 0.281 ± 0.011 | 0.213 ± 0.011 | 0.217 ± 0.010 | 0.234 ± 0.018 |

At the end of the study, mice were sacrificed and muscle mass was assessed by dissecting and weighing the gastrocnemius and quadriceps. Results are shown in Table 5. To confirm biological activity of prednisone, sera from a separate cohort of mice were collected and analyzed for IL6 and IL1β (Ani Lyctics, Inc., Gaithersburg, Md.). Both cytokines were found to be reduced in the sera of mice treated with prednisone.

TABLE 5

Muscle weight (average ± SEM, g)

| Muscle | Prednisone + JA-16 (mdx) | Prednisone (mdx) | vehicle control (mdx) | vehicle control (non-mdx) |
|---|---|---|---|---|
| Gastroc | 0.364 ± 0.019 | 0.287 ± 0.023 | 0.299 ± 0.019 | 0.280 ± 0.010 |
| Quad | 0.527 ± 0.030 | 0.417 ± 0.029 | 0.415 ± 0.030 | 0.392 ± 0.010 |

Therefore, the results demonstrate that in muscular dystrophy, administration of an inhibitor of GDF-8, i.e., anti-GDF-8 antibody, and prednisone is effective in increasing muscle mass and strength relative to treatment with prednisone alone or vehicle.

Furthermore, in these studies the effects of JA16 plus prednisone treatment (Example 2) were greater than the effects of treatment with JA16 alone (Example 1). The increase in body weight compared to vehicle after four weeks of treatment was more dramatic for JA16 plus prednisone treatment than for JA16 treatment alone. The increase in grip strength compared to vehicle control after four weeks of treatment with JA16 plus prednisone was greater that the increase after six or ten weeks of treatment with JA16 alone. The increase over vehicle control in muscle mass after four weeks of treatment with JA16 plus prednisone was also greater than the increase after twelve weeks of treatment with JA16 alone.

Example 3

Effect of GDF-8 Neutralizing Antibody on Prednisone-Induced Muscle Atrophy

Figure 1A:
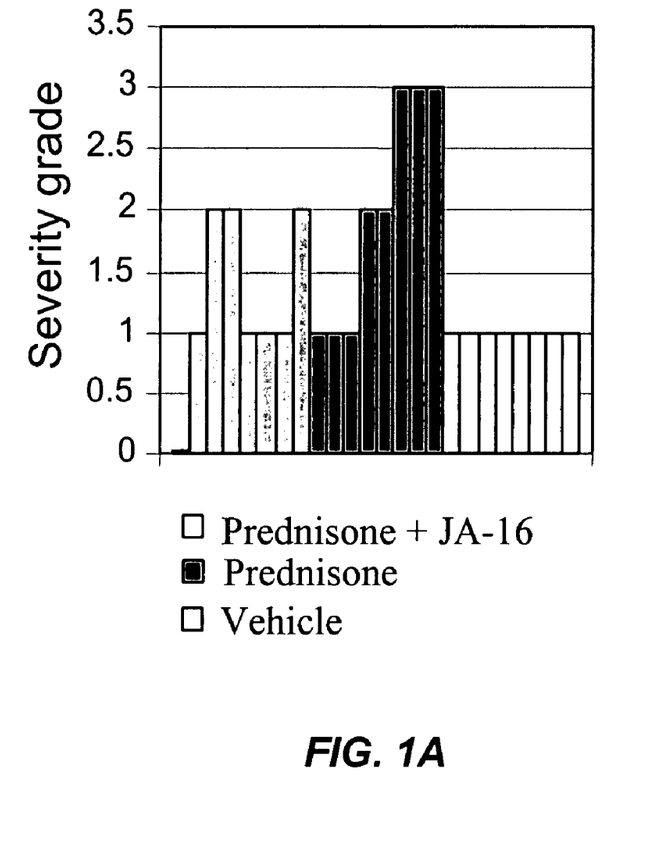
FIG. 1A shows severity of muscle fiber atrophy on a 0-4 scale at the end of the trial.
Figure 1B:
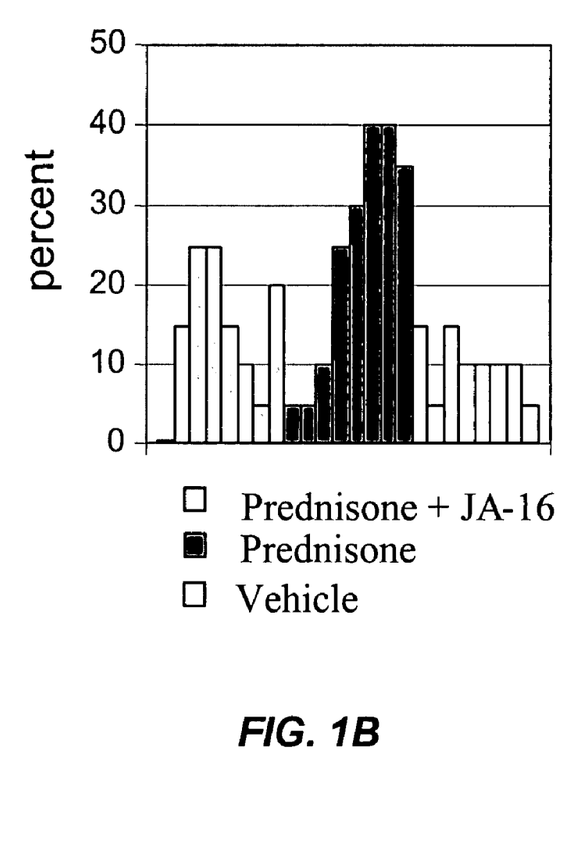
FIG. 1B shows percentage of affected (atrophied) muscle fibers at the end of the trial. Each bar represents a single mouse.

In the mice treated as described in Example 2, diaphragm muscle was histologically examined as described in Example 1. The morphological changes were evaluated by an independent pathology lab that had no knowledge of the treatment group assignments. Severity grades were assigned on a scale from 0 to 4 (0=none; 1=minimal; 2=mild; 3=moderate; and 4=marked). Results are shown in FIG. 1A (severity scores) and FIG. 1B (percentage of muscle fibers atrophied). The results show that administration of the anti-GDF-8 antibody with prednisone reduces prednisone-induced muscle atrophy.

Example 4

Treatment of Muscular Dystrophies

As an example of treating MD in humans, the Myo29 antibody is administered in combination with prednisone or prednisolone. Nonlimiting exemplary treatment regimens and outcomes are summarized in Table 6. Other treatment regimens can be determined by a treating physician, with ranges of the corticosteroids and GDF-8 inhibitors dosage and administration as discussed above.

TABLE 6

| Patient No. | Treatment Regimen | Treatment Goal |
|---|---|---|
| Patient 1 | Myo29 at 10 mg/kg/week, administered by bi-weekly injection plus prednisone at 0.75 mg/kg/day for 2 years, or continuing treatment as needed | Maintenance and/or increase of muscle mass, strength, and function over benefit of prednisone alone |
| Patient 2 | Myo29 at 0.1 mg/kg/week, administered by weekly IV plus prednisone at 1.0 mg/kg/day, continuing treatment as needed. | Maintenance and/or increase of muscle mass, strength, and function over benefit of prednisone alone |
| Patient 3 | Myo29 at 1 mg/kg/week administered by monthly injection plus prednisone at 0.50 mg/kg/day for 2 years, or continuing treatment as needed | Maintenance and/or increase of muscle mass, strength and function or increased preservation of function for muscle groups that are not already compromised over benefit of prednisone alone |
| Patient 4 | Myo29 at 20 mg/kg/week, administered in a single dose by IV plus prednisone at 0.75 mg/kg/day for 2 years, or continuing treatment as needed | Maintenance and/or increase of muscle mass, strength and function or increased preservation of function over benefit of prednisone alone |
| Patient 5 | Myo29 at .1 mg/kg/week, administered in a single dose by IV plus prednisone at 5 mg/kg/wk, as needed | Maintenance and/or increase of muscle mass, strength and function over benefit of prednisone alone |
| Patient 6 | Myo29 at 1 mg/kg/week, administered weekly by IV plus prednisone at 2 mg/kg/wk for at least 2 months, or as needed | Maintenance and/or increase of muscle mass, strength and function over benefit of prednisone alone |
| Patient 7 | Myo29 at 10 mg/kg/week, administered in a single dose by subcutaneous injection plus prednisone at 7 mg/kg/wk for at least 6 months, or continuing treatment as needed | Maintenance and/or increase of muscle mass, strength and function over benefit of prednisone alone |
| Patient 8 | Myo29 at 20 mg/kg/week, administered weekly by | Maintenance and/or increase of muscle mass, strength and |

TABLE 6-continued

| Patient No. | Treatment Regimen | Treatment Goal |
|---|---|---|
| | injection plus prednisone at 14 mg/kg/wk for 2 years, or continuing treatment as needed | function over benefit of prednisone alone |
| Patient 9 | Myo29 at 1 mg/kg/week, administered bi-monthly by IV plus prednisone at 10 mg/kg/wk for at least 1 month, or continuing treatment as needed | Maintenance and/or increase of muscle mass, strength and function over benefit of prednisone alone |
| Patient 10 | Myo29 at 0.3 mg/kg/week, administered monthly by subcutaneous injection plus prednisone at 0.75 mg/kg/day for 1 year, or continuing treatment as needed | Maintenance and/or increase of muscle mass, strength and function or increased preservation of function for muscle groups over benefit of prednisone alone |

All publications and patents cited and sequences identified by accession or database reference numbers in this disclosure are incorporated by reference in their entirety.

The invention claimed is:

1. A method of treating a mammal with a decrease in muscle strength or muscle mass, comprising administering to the mammal a therapeutically effective amount of at least one Growth and Differentiation Factor-8 (GDF-8) inhibitor and a therapeutically effective amount of at least one corticosteroid in the amounts and for a period of time sufficient to treat a decrease in muscle strength or muscle mass.

2. The method of claim 1, wherein the decrease in muscle strength or muscle mass is evaluated by at least one parameter chosen from muscle mass, muscle contraction force, serum creatine kinase (CK) concentration, or muscle morphology.

3. The method of claim 1, wherein the muscle is chosen from at least one of gastrocnemius, tibialis anterior, quadriceps, extensor digitorum longus, cardiac muscle, or diaphragm muscle.

4. The method of claim 1, wherein treating said mammal results in increased body weight of said mammal.

5. The method of claim 1, wherein treating said mammal results in increased grip strength.

6. The method of claim 1, wherein the mammal is human.

7. The method of claim 1, wherein the corticosteroid is chosen from at least one of:
(a) at least one of beclomethasone dipropionate, budesonide, cortisol, dexamethasone, fluticason propionate, mometasone furoate, prednisone, or triamcinolone acetonide;
(b) a derivative of at least one of beclomethasone dipropionate, budesonide, cortisol, dexamethasone, fluticason propionate, mometasone furoate, prednisone, or triamcinolone acetonide; or
(c) a pharmaceutically acceptable salt of at least one of beclomethasone dipropionate, budesonide, cortisol, dexamethasone, fluticason propionate, mometasone furoate, prednisone, or triamcinolone acetoniden.

8. The method of claim 1, wherein the corticosteroid is prednisone or prednisolone.

9. The method of claim 1, wherein the corticosteroid is administered at a dose between 0.1 and 2.0 mg/kg/day.

10. The method of claim 1, wherein the corticosteroid is administered orally.

11. The method of claim 1, wherein the method results in treating of cardiomyopathy of said mammal.

12. The method of claim 1, wherein the administration of GDF-8 inhibitor and corticosteroid is concurrent.

13. The method of claim 1, wherein the administration of GDF-8 inhibitor and corticosteroid is consecutive.

14. The method of claim 1, wherein the GDF-8 inhibitor is chosen from an antibody to GDF-8, an antibody to a GDF-8 receptor, a soluble GDF-8 receptor, a GDF-8 propeptide, follistatin, or a follistatin-domain-containing protein.

15. The method of claim 14, wherein the antibody to GDF-8 is chosen from JA-16, Myo29, Myo28, or Myo22.

16. The method of claim 14, wherein the GDF-8 propeptide is mutated at an aspartate residue.

17. The method of claim 14, wherein the GDF-8 propeptide is joined to the Fc portion of an immunoglobulin.

18. The method of claim 14, wherein the GDF-8 receptor is ActRIIB.

19. The method of claim 14, wherein the GDF-8 receptor is joined to the Fc portion of an immunoglobulin.

20. The method of claim 14, wherein the GDF-8 inhibitor is follistatin.

21. The method of claim 14, wherein the follistatin-domain-containing protein is GASP-1.

22. A method of treating muscle weakness, comprising administering to a mammal a therapeutically effective amount of at least one GDF-8 inhibitor and a therapeutically effective amount of at least one corticosteroid in the amounts and for a period of time sufficient to treat loss of muscle strength.

23. The method of claim 22, wherein the mammal is human.

24. The method of claim 22, wherein the corticosteroid is chosen from at least one of:
(a) at least one of beclomethasone dipropionate, budesonide, cortisol, dexamethasone, fluticason propionate, mometasone furoate, prednisone, or triamcinolone acetonide;
(b) a derivative of at least one of beclomethasone dipropionate, budesonide, cortisol, dexamethasone, fluticason propionate, mometasone furoate, prednisone, or triamcinolone acetonide; or
(c) a pharmaceutically acceptable salt of at least one of beclomethasone dipropionate, budesonide, cortisol, dexamethasone, fluticason propionate, mometasone furoate, prednisone, or triamcinolone acetoniden.

25. The method of claim 22, wherein the corticosteroid is prednisone or prednisolone.

26. The method of claim 22, wherein the corticosteroid is administered at a dose between 0.1 and 2.0 mg/kg/day.

27. The method of claim 22, wherein the corticosteroid is administered orally.

28. The method of claim 22, wherein the GDF-8 inhibitor is chosen from an antibody to GDF-8, an antibody to a GDF-8 receptor, a soluble GDF-8 receptor, a GDF-8 propeptide, follistatin, or a follistatin-domain-containing protein.

29. The method of claim 28, wherein the antibody to GDF-8 is chosen from JA-16, Myo29, Myo28, or Myo22.

30. The method of claim 28, wherein the GDF-8 propeptide is mutated at an aspartate residue.

31. The method of claim 28, wherein the GDF-8 propeptide is joined to the Fc portion of an immunoglobulin.

32. The method of claim 28, wherein the GDF-8 receptor is ActRIIB.

33. The method of claim 28, wherein the GDF-8 receptor is joined to the Fc portion of an immunoglobulin.

34. The method of claim 28, wherein the GDF-8 inhibitor is follistatin.

35. The method of claim 28, wherein the follistatin-domain-containing protein is GASP-1.

36. A method of treating corticosteroid-induced muscle atrophy in a mammal that is currently undergoing corticosteroid therapy, comprising administering to a mammal a therapeutically effective amount of at least one GDF-8 inhibitor.

37. The method of claim 36, wherein the mammal is human.

38. The method of claim 36, wherein the corticosteroid is chosen from at least one of:
   (a) at least one of beclomethasone dipropionate, budesonide, cortisol, dexamethasone, fluticason propionate, mometasone furoate, prednisone, or triamcinolone acetonide;
   (b) a derivative of at least one of beclomethasone dipropionate, budesonide, cortisol, dexamethasone, fluticason propionate, mometasone furoate, prednisone, or triamcinolone acetonide; or
   (c) a pharmaceutically acceptable salt of at least one of beclomethasone dipropionate, budesonide, cortisol, dexamethasone, fluticason propionate, mometasone furoate, prednisone, or triamcinolone acetoniden.

39. The method of claim 36, wherein the corticosteroid is prednisone or prednisolone.

40. The method of claim 36, wherein the corticosteroid is administered at a dose between 0.1 and 2.0 mg/kg/day.

41. The method of claim 36, wherein the corticosteroid is administered orally.

42. The method of claim 36, wherein the GDF-8 inhibitor is chosen from an antibody to GDF-8, an antibody to a GDF-8 receptor, a soluble GDF-8 receptor, a GDF-8 propeptide, follistatin, or a follistatin-domain-containing protein.

43. The method of claim 42, wherein the antibody to GDF-8 is chosen from JA-16, Myo29, Myo28, or Myo22.

44. The method of claim 42, wherein the GDF-8 propeptide is mutated at an aspartate residue.

45. The method of claim 42, wherein the GDF-8 propeptide is joined to the Fc portion of an immunoglobulin.

46. The method of claim 42, wherein the GDF-8 receptor is ActRIIB.

47. The method of claim 42, wherein the GDF-8 receptor is joined to the Fc portion of an immunoglobulin.

48. The method of claim 42, wherein the GDF-8 inhibitor is follistatin.

49. The method of claim 42, wherein the follistatin-domain-containing protein is GASP-1.

50. A method of treating a neuromuscular disorder, comprising administering to a mammal having the neuromuscular disorder a therapeutically effective amount of at least one GDF-8 inhibitor and a therapeutically effective amount of at least one corticosteroid in the amounts and for a period of time sufficient to treat the neuromuscular disorder.

51. The method of claim 50, wherein the neuromuscular disorder is a muscular dystrophy.

52. The method of claim 51, wherein the muscular dystrophy is Duchenne muscular dystrophy.

53. The method of claim 51, wherein the muscular dystrophy is Becker muscular dystrophy.

54. The method of claim 50, wherein the mammal is human.

55. The method of claim 50, wherein the corticosteroid is chosen from at least one of:
   (a) at least one of beclomethasone dipropionate, budesonide, cortisol, dexamethasone, fluticason propionate, mometasone furoate, prednisone, or triamcinolone acetonide;
   (b) a derivative of at least one of beclomethasone dipropionate, budesonide, cortisol, dexamethasone, fluticason propionate, mometasone furoate, prednisone, or triamcinolone acetonide; or
   (c) a pharmaceutically acceptable salt of at least one of beclomethasone dipropionate, budesonide, cortisol, dexamethasone, fluticason propionate, mometasone furoate, prednisone, or triamcinolone acetoniden.

56. The method of claim 50, wherein the corticosteroid is prednisone or prednisolone.

57. The method of claim 50, wherein the corticosteroid is administered at a dose between 0.1 and 2.0 mg/kg/day.

58. The method of claim 50, wherein the corticosteroid is administered orally.

59. The method of claim 50, wherein the GDF-8 inhibitor is chosen from an antibody to GDF-8, an antibody to a GDF-8 receptor, a soluble GDF-8 receptor, a GDF-8 propeptide, follistatin, or a follistatin-domain-containing protein.

60. The method of claim 59, wherein the antibody to GDF-8 is chosen from JA-16, Myo29, Myo28, or Myo22.

61. The method of claim 59, wherein the GDF-8 propeptide is mutated at an aspartate residue.

62. The method of claim 59, wherein the GDF-8 propeptide is joined to the Fc portion of an immunoglobulin.

63. The method of claim 59, wherein the GDF-8 receptor is ActRIIB.

64. The method of claim 59, wherein the GDF-8 receptor is joined to the Fc portion of an immunoglobulin.

65. The method of claim 59, wherein the GDF-8 inhibitor is follistatin.

66. The method of claim 59, wherein the follistatin-domain-containing protein is GASP-1.

67. The method of claim 59, wherein the method results in treating of cardiomyopathy of said mammal.

68. The method of claim 59, wherein the administration of GDF-8 inhibitor and corticosteroid is concurrent.

69. The method of claim 59, wherein the administration of GDF-8 inhibitor and corticosteroid is consecutive.

* * * * *